US00PP26050P2

(12) United States Plant Patent
Uebelhart

(10) Patent No.: US PP26,050 P2
(45) Date of Patent: Nov. 3, 2015

(54) ***GAILLARDIA* PLANT NAMED 'SUNNY WHEELER'**

(50) Latin Name: *Gaillardia aristata*
Varietal Denomination: Sunny Wheeler

(71) Applicant: Georg G. Uebelhart, Schwarmstedt (DE)

(72) Inventor: Georg G. Uebelhart, Schwarmstedt (DE)

(73) Assignee: JELITTO STAUDEN SAMEN GMBH, Schwarmstedt (DE)

( * ) Notice: Subject to any disclaimer, the term of this patent is extended or adjusted under 35 U.S.C. 154(b) by 83 days.

(21) Appl. No.: 13/999,512

(22) Filed: Mar. 5, 2014

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Susan McCormick Ewoldt
(74) *Attorney, Agent, or Firm* — Penny J. Aguirre

(57) ABSTRACT

A new cultivar of *Gaillardia*, 'Sunny Wheeler', characterized by its medium sized inflorescences with ray florets with fluted petals that are bright yellow in color with a slight blush of red at the base, its reliably perennial habit with hardiness in U.S.D.A. Zones 3 to 9, its dwarf, spreading plant habit, and its long blooming period with numerous blooms throughout the growing season.

2 Drawing Sheets

Botanical classification: *Gaillardia aristata.*
Variety denomination: 'Sunny Wheeler'.

CROSS REFERENCE TO RELATED APPLICATIONS

This application is co-pending with a U.S. Plant Patent Applications filed for plants derived from the Inventor's breeding program that are entitled *Gaillardia* Plant Named 'Fancy Wheeler' (U.S. Plant Pat. No. 22,016), 'Lucky Wheeler' (U.S. Plant Pat. No. 23,544), and *Gaillardia* Plant Named 'Jazzy Wheeler' (U.S. Plant Pat. No. 22,217).

BACKGROUND OF THE INVENTION

The present invention relates to a new and distinct cultivar of *Gaillardia* plant, botanically known as *Gaillardia aristata* 'Sunny Wheeler' and will be referred to hereinafter by its cultivar name, 'Sunny Wheeler'.

'Sunny Wheeler' was derived from a controlled breeding program conducted by the Inventor at his nursery in Schwamstedt, Germany. The breeding program focuses on obtaining new cultivars of *Gaillardia* with compact and floriferous plant habit in a range of flower colors. In summer 2009, the Inventor made a cross between unnamed plants from his breeding program as both the female and male parents (sowing no. G10004). Sunny Wheeler' was selected in 2010 by the Inventor as a single unique plant from the resulting seedlings.

Asexual propagation of the new cultivar was first accomplished under the direction of the Inventor by in vitro propagation in Rijswijk, The Netherlands in 2010. Asexual propagation by stem cuttings and tissue culture has determined that the characteristics of the new cultivar are stable and are reproduced true to type in successive generations.

SUMMARY OF THE INVENTION

The following traits have been repeatedly observed and are determined to be the characteristics of the new cultivar of

*Gaillardia*. These attributes in combination distinguish 'Sunny Wheeler' as unique from all other varieties of *Gaillardia* known to the Inventor.

1. 'Sunny Wheeler' exhibits medium sized inflorescences with ray florets with fluted petals that are bright yellow in color with a slight blush of red at the base.
2. 'Sunny Wheeler' is reliably perennial and hardy in U.S.D.A. Zones 3 to 9.
3. 'Sunny Wheeler' exhibits a dwarf, spreading plant habit.
4. 'Sunny Wheeler' produces numerous blooms throughout the growing season.

Both the male and female parents of 'Sunny Wheeler' differ from 'Sunny Wheeler' in having more red coloration to the petals (less yellow). 'Sunny Wheeler' can also be most close compared to cultivars from the same breeding program 'Fancy Wheeler', 'Lucky Wheeler' and 'Jazzy Wheeler'. They are all three similar in having a dwarf, spreading plant habit. 'Fancy Wheeler' differs from 'Sunny Wheeler' in having larger inflorescences with ray florets that have red centers and yellow tips and lack fluted petals. 'Jazzy Wheeler' differs from 'Sunny Wheeler' in having inflorescences with ray florets that have yellow-orange centers and yellow tips and in lacking fluted petals. 'Lucky Wheeler' is similar to 'Sunny Wheeler' in having inflorescences with fluted ray florets but differs from 'Sunny Wheeler' in having inflorescences with ray florets that have red centers and yellow tips (bicolor).

BRIEF DESCRIPTION OF THE DRAWINGS

The accompanying colored photographs illustrate the overall appearance and distinct characteristics of the new *Gaillardia*. The photographs were taken of a plant about 14-months in age as grown outdoors in a 10-liter container in Schwamstedt, Germany.

The photograph in FIG. 1 provides a close-up view of inflorescences of 'Sunny Wheeler' when newly open and the photograph in FIG. 2 provides a view of the plant habit of 'Sunny Wheeler'.

Figure 1:
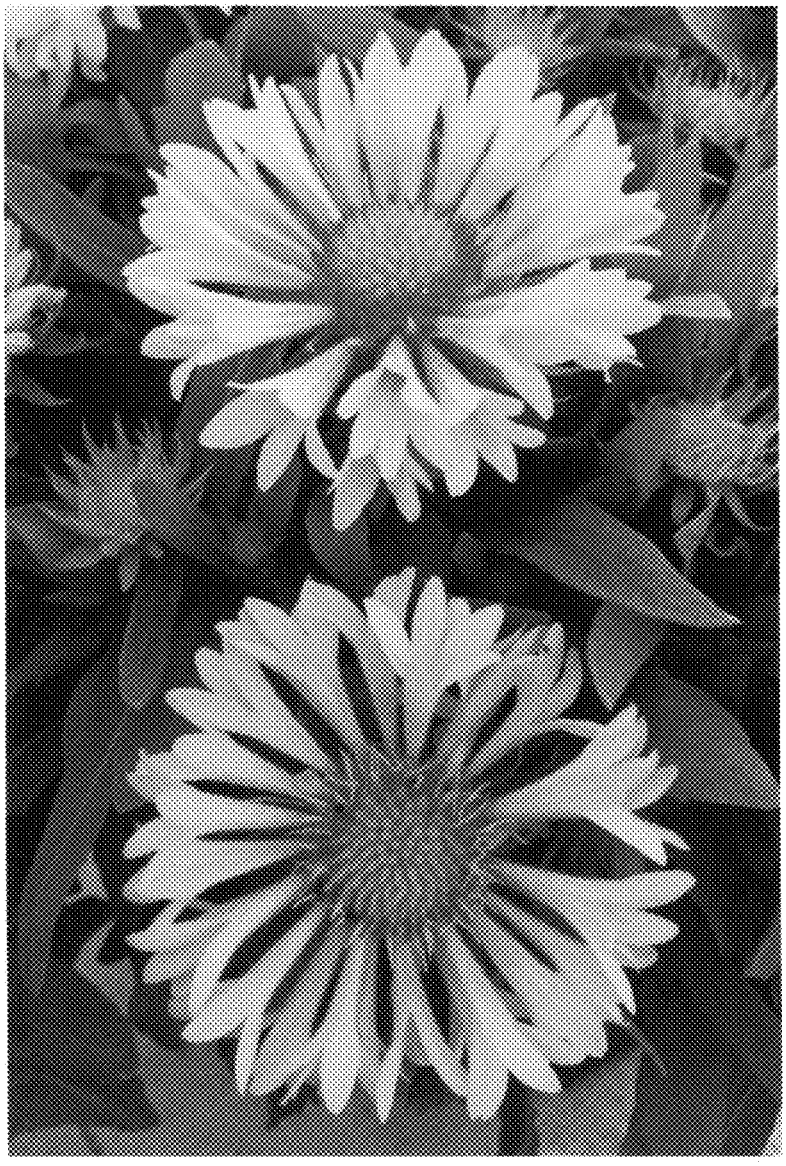
Figure 2:
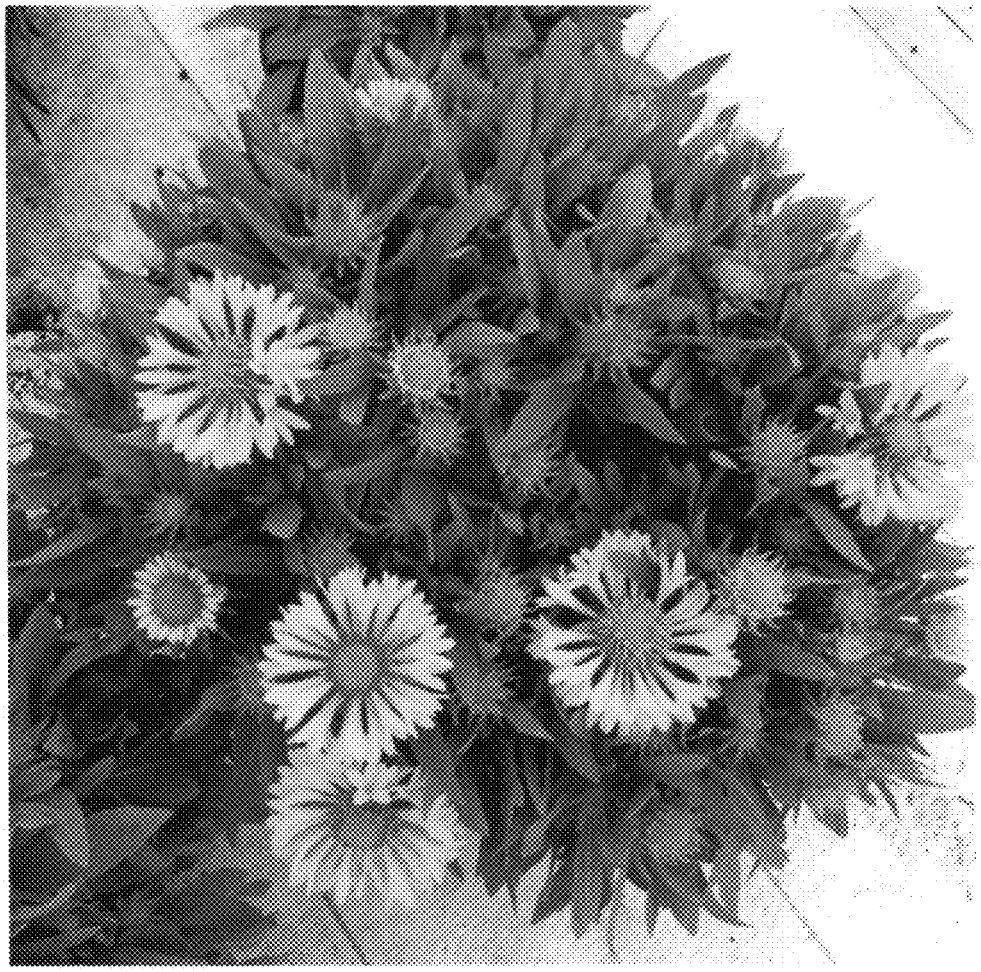

The colors in the photographs are as close as possible with the digital photography and printing techniques utilized and the color codes in the detailed botanical description accurately describe the colors of the new *Gaillardia*.

DETAILED BOTANICAL DESCRIPTION

The detailed botanical data was collected from plants about 14-months in age as grown in 10-liter containers in an unheated greenhouse in Schwamstedt, Germany. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—Continuously from mid spring to early October in The Netherlands.

*Plant type*.—Herbaceous perennial.

*Plant habit*.—Dwarf and spreading growth habit.

*Height and spread*.—About 25 cm in height and 45 cm in width as grown in a 10-liter container.

*Hardiness*.—U.S.D.A. Zones 3 to 9.

*Diseases resistance*.—No susceptibility or resistance to diseases has been observed.

*Root description*.—Fibrous.

*Propagation*.—Stem cuttings and tissue culture.

*Crop maintenance*.—No pinching or pruning required.

*Growth rate*.—Low to moderate, 5 cm per month.

Stem description:

*Stem shape*.—Rounded.

*Stem aspect*.—Erect to 60° from horizontal.

*Stem strength*.—Strong.

*Stem color*.—138A to 138B.

*Stem surface*.—Densely covered with strigose hairs averaging 1 mm in length and NN155D in color, rough to touch.

*Lateral branch length*.—Average of 8 cm (excluding peduncles).

*Lateral branch diameter*.—Average of 3 mm.

*Quantity of lateral branches*.—About 8 per plant in a 1.5-liter container.

*Internode length*.—Average of 1.2 cm.

*Branching*.—Freely branched.

Foliage description:

*Leaf division*.—Simple.

*Leaf shape*.—Oblanceolate to linear oblong.

*Leaf base*.—Decurrent.

*Leaf apex*.—Acute.

*Leaf margin*.—Entire.

*Leaf venation*.—Pinnate, 138A in color on upper and lower surface.

*Leaf attachment*.—Sessile.

*Leaf arrangement*.—Alternate.

*Leaf surface*.—Upper and lower surfaces; dull, rough to touch, and moderately covered with strigose hairs about 0.5 mm in length and NN155D in color.

*Leaf color*.—Young foliage; upper surface 144A, lower surface 138A to 138B, mature foliage; upper surface 138A and lower surface a blend of 138B and 144A.

*Leaf size*.—Average of 8 cm in length and 1.8 cm in width.

Flower description:

*Inflorescence type*.—Terminal capitulum with many disc florets, one row of ray florets with fluted petals, and three rows of involucral bracts.

*Rate of flowering*.—Terminal inflorescence opens before lateral inflorescence.

*Lastingness of inflorescence*.—About 2 weeks, persistent.

*Inflorescence aspect*.—Held upright.

*Fragrance*.—Moderate in strength, slightly sweet, chrysanthemum-like.

*Quantity of inflorescences*.—About 40 per plant in a 1.5-liter container.

*Inflorescence buds*.—About 7 mm in depth and 1.3 mm in diameter, flattened globular, color N144A to N144B with center 151D.

*Inflorescence size*.—Average of 3.1 cm in depth and 6 to 7 cm in diameter, diameter of disk about 2.3 cm.

*Receptacle*.—Flattened globular in shape, about 3 mm in depth, 4 mm in diameter, 155D in color.

*Peduncle*.—Round in shape, upright, moderately strong, 138A to 138B, about 4.6 cm in length and 2 mm in diameter, slightly pubescent with soft hairs 0.5 mm in length and NN155D in color.

*Involucral bracts (phyllaries)*.—Average of 38 per inflorescence, arranged in 3 rows, lanceolate to narrowly ovate in shape, narrowly acute apex, broadly cuneate base, margin entire and covered in villous hairs 1.5 mm in length NN155D in color, upper surface dull and smooth and lower surface dull and densely covered with short hairs; about 0.5 mm in length and 157D in color, 138A to 138B in color, about 1.1 cm in length and 2 mm in width.

Ray florets (pistillate):

*Number*.—Average of 18.

*Arrangement*.—Rotate, 1 whorl.

*Shape*.—Fluted into 5-segments, segments elliptic with lower half fused into tube.

*Aspect*.—Outward to slightly upward at an angle of 25° from horizontal.

*Size*.—Average of 3 cm in length and 9 mm in width.

*Petal apex*.—Rounded.

*Petal base*.—Tubular.

*Petal margins*.—Segment margins entire.

*Petal surface*.—Upper surface smooth, lower surface moderately covered with short hairs about 0.8 mm in length.

*Petal color*.—Opening; upper and lower surface 13A to 13C, fully open; upper and lower surface a blend of 13B and 23A suffused with N30A at the base.

Disk florets (perfect):

*Quantity*.—Average of 120.

*Shape*.—Tubular with upper 30% free.

*Arrangement*.—Spiral concentric towards center of disc.

*Size*.—About 8 mm in length and 3 mm in width.

*Petal apex*.—Free, narrowly acute, entire margin.

*Petal base*.—Fused.

*Petal texture*.—Upper surface; smooth, slightly glossy, lower surface; strongly hirsute with hairs about 0.7 mm in length, slightly glossy.

*Color*.—When opening upper and lower surface; tip 34A, mid-section 21B and base 145A, mature upper and lower surface; tip N30A to N30C, mid-section 21B and base 145A to 145C.

Reproductive organs:

*Presence*.—Disk flowers are perfect, ray flowers are (pistillate).

*Gynoecium*.—1 pistil per disk and ray floret, 1.1 cm in length, stigma decurrent and 53A in color, style 6 mm in length and 150D in color, ovary 145D in color.

*Androecium*.—5 stamen per disk floret, filament 3 mm in length and 157D in color, anther linear in shape, about 4 mm in length and 13B in color with apex 202A, pollen moderate in quantity and 14B in color.

*Fruit and seed*.—No fruits or seeds observed to date.

It is claimed:

1. A new and distinct variety of *Gaillardia* plant named 'Sunny Wheeler' as described and illustrated herein.

* * * * *